US00PP30215P3

(12) United States Plant Patent
Levac

(10) Patent No.: US PP30,215 P3
(45) Date of Patent: Feb. 19, 2019

(54) ***THUNBERGIA* PLANT NAMED 'DL1501'**

(50) Latin Name: *Thunbergia alata*
Varietal Denomination: DL1501

(71) Applicant: Denis Levac, St. Paul de Jolliette (CA)

(72) Inventor: Denis Levac, St. Paul de Jolliette (CA)

( * ) Notice: Subject to any disclaimer, the term of this patent is extended or adjusted under 35 U.S.C. 154(b) by 15 days.

(21) Appl. No.: 15/731,523

(22) Filed: Jun. 21, 2017

(65) Prior Publication Data

US 2018/0376643 P1 Dec. 27, 2018

(51) Int. Cl.
*A01H 5/02* (2018.01)

(52) U.S. Cl.
USPC ..... Plt./226

(58) Field of Classification Search
None
See application file for complete search history.

(56) References Cited

PUBLICATIONS

UPOV hit on *Thunbergia* plant named 'DL1501', Ca PBR 17-9105, filed Feb. 21, 2017.*

* cited by examiner

*Primary Examiner* — Anne Marie Grunberg
(74) *Attorney, Agent, or Firm* — C. A. Whealy

(57) ABSTRACT

A new and distinct cultivar of *Thunbergia* plant named 'DL1501', characterized by its upright and vining plant habit; freely branching habit; dense and bushy plant form; freely flowering habit; large yellow orange and greyed orange bi-colored flowers; and good garden performance.

1 Drawing Sheet

Botanical designation: *Thunbergia alata.*
Cultivar denomination: 'DL1501'.

BACKGROUND OF THE INVENTION

The present invention relates to a new and distinct cultivar of *Thunbergia* plant, botanically known as *Thunbergia alata*, and hereinafter referred to by the name 'DL1501'.

The new *Thunbergia* plant is a naturally-occurring branch mutation of *Thunbergia alata* 'Arizona Glow', not patented. The new *Thunbergia* plant was discovered and selected by the Inventor on a single flowering plant within a population of plants of 'Arizona Glow' in a controlled greenhouse environment in L'Assomption, Quebec, Canada in March, 2015.

Asexual reproduction of the new *Thunbergia* plant by terminal cuttings in a controlled greenhouse environment in Sainte-Adèle, Quebec, Canada since April, 2015 has shown that the unique features of this new *Thunbergia* plant are stable and reproduced true to type in successive generations.

SUMMARY OF THE INVENTION

Plants of the new *Thunbergia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DL1501'. These characteristics in combination distinguish 'DL1501' as a new and distinct *Thunbergia* plant:

1. Upright and vining plant habit.
2. Freely branching habit; dense and bushy plant form.

3. Freely flowering habit.
4. Large yellow orange and greyed orange bi-colored flowers.
5. Good garden performance.

Plants of the new *Thunbergia* can be compared to plants of the mutation parent, 'Arizona Glow'. Plants of the new *Thunbergia* differ from plants of 'Arizona Glow' primarily in flower color as plants of 'Arizona Glow' have orange and dark reddish orange-colored flowers.

Plants of the new *Thunbergia* can be compared to plants of *Thunbergia alata* 'Orange Wonder', disclosed in U.S. Plant Pat. No. 14,767. In side-by-side comparisons, plants of the new *Thunbergia* differ primarily from plants of 'Orange Wonder' in flower color as plants of 'Orange Wonder' have bright orange-colored flowers.

Plants of the new *Thunbergia* can be compared to plants of *Thunbergia alata* 'Lemon Star', disclosed in U.S. Plant Pat. No. 14,371. In side-by-side comparisons, plants of the new *Thunbergia* differ primarily from plants of 'Lemon Star' in flower color as plants of 'Lemon Star' have bright yellow-colored flowers.

BRIEF DESCRIPTION OF THE PHOTOGRAPHS

The accompanying colored photographs illustrate the overall appearance of the new *Thunbergia* plant showing the colors as true as it is reasonably possible to obtain in colored reproductions of this type. Colors in the photographs may differ slightly from the color values cited in the detailed botanical description which accurately describe the actual colors of the new *Thunbergia* plant.

The photograph at the top of the sheet comprises a side perspective view of a typical flowering plant of 'DL1501' grown in a container.

The photograph at the bottom of the sheet is a close-up view of a typical flowering plant of 'DL1501'.

DETAILED BOTANICAL DESCRIPTION

The aforementioned photographs and following observations and measurements describe plants grown during the early spring in one-gallon containers in an acrylic-covered greenhouse in Carleton, Mich. and under cultural practices typical of commercial *Thunbergia* production. During the production of the plants, day and night temperatures ranged from 18° C. to 27° C. Plants were 13 weeks old when the photographs and description were taken. In the following description, color references are made to The Royal Horticultural Society Colour Chart, 2007 Edition, except where general terms of ordinary dictionary significance are used.

Botanical classification: *Thunbergia alata* 'DL1501'.

Parentage: Naturally-occurring branch mutation of *Thunbergia alata* 'Arizona Glow', not patented.

Propagation:

*Type*.—By terminal cuttings.

*Time to initiate roots, summer*.—About four to five days at temperatures about 18° C. to 25° C.

*Time to initiate roots, winter*.—About five to six days at temperatures about 18° C. to 24° C.

*Time to develop roots, summer*.—About three weeks at temperatures about 18° C. to 25° C.

*Time to develop roots, winter*.—About four weeks at temperatures about 18° C. to 24° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright and vining plant habit; plants require support; vigorous growth habit; moderately rapid to rapid growth rate.

*Branching habit*.—Freely branching habit with about ten primary lateral branches with secondary laterals potentially developing at every node; bushy and dense appearance.

*Plant height*.—About 117 cm.

*Plant diameter* (*area of spread*).—About 38 cm.

Lateral branch description:

*Length*.—About 65 cm.

*Diameter*.—About 2 mm.

*Internode length*.—About 16.5 cm.

*Texture and luster*.—Pubescent, coarse; matte.

*Strength*.—Moderately strong, flexible.

*Color, developing*.—Close to 146B to 146C.

*Color, fully developed*.—Close to 146A; stems exposed to sunlight are tinted with close to 187A.

Leaf description:

*Arrangement*.—Opposite, simple.

*Length*.—About 10.8 cm.

*Width*.—About 8.2 cm.

*Shape*.—Sagittate.

*Apex*.—Acute.

*Base*.—Sagittate.

*Margin*.—Entire with very shallow irregular lobes.

*Aspect*.—Horizontal to somewhat downward.

*Texture and luster, upper and lower surfaces*.—Pubescent; matte.

*Venation pattern*.—Pinnate.

*Color*.—Developing leaves, upper surface: Close to 146B. Developing leaves, lower surface: Close to 146D. Fully developed leaves, upper surface: Close to 137A; venation, close to 147B. Fully developed leaves, lower surface: Close to 147B; venation, close to 147C.

*Petioles*.—Length: About 5.5 cm. Diameter: About 7 mm. Texture and luster, upper and lower surfaces: Pubescent, rough; matte. Color, upper surface: Close to 146A. Color, lower surface: Close to 146B.

Flower description:

*Flower type and habit*.—Single axillary salverform flowers; freely flowering habit with numerous flowers developing per plant; flowers face mostly outwardly.

*Natural flowering season*.—Plants flower continuously from April until frost in Michigan; plants begin flowering about six weeks after planting.

*Flower longevity*.—Flowers last about five to seven days on the plant; petals not persistent and sepals persistent.

*Fragrance*.—None detected.

*Flower diameter*.—About 4.3 cm.

*Flower length* (*height*).—About 3.5 cm.

*Throat diameter*.—About 1.1 cm.

*Tube length*.—About 2.3 cm.

*Tube diameter*.—About 4 mm.

*Flower buds*.—Length: About 2.8 cm. Diameter: About 1.6 cm. Shape: Elliptical to slightly cordate. Color: Close to 16D.

*Petals*.—Quantity and arrangement: Corolla consists of five petals in a single whorl and fused towards the base. Lobe length: About 1.7 cm. Lobe width: About 1.8 cm. Lobe shape: Fan-shaped. Lobe apex: Mostly rounded and shallowly emarginate. Lobe margin: Entire; undulate. Lobe texture and luster, upper and lower surfaces: Smooth, glabrous, velvety; matte. Throat texture: Minute pubescence. Tube texture: Scattered pubescence. Color: When opening, upper surface: Close to 21B to 21C. When opening, lower surface: Close to 22D. Fully opened, upper surface: Ground color, close to 23B overlain with a broad star-shaped pattern, close to N167B to N167C; faint central nectar guides, close to 175B; venation, similar to lamina colors; with development, ground color becoming closer to 23C, star-shaped pattern becoming closer to 167C and nectar guides becoming closer to 174A. Fully opened, lower surface: Close to 173D; venation, close to N186A; color becoming closer to 24D with development. Throat: Close to N186A; venation, close to N186A. Tube: Close to N187B to N187C tinted with close to N186B; venation, close to N186B.

*Sepals*.—Quantity and arrangement: About 16 to 18 in a single whorl; fused at the base. Length: About 2 mm. Width: Less than 1 mm. Shape: Lanceolate. Apex: Acute. Margin: Entire. Texture and luster, upper and lower surfaces: Minute pubescence; matte. Color, upper and lower surfaces: Close to 145B to 145C.

*Flower bracts*.—Quantity and arrangement: Two, opposite. Length: About 2 cm. Width: About 1.6 cm. Shape: Cordate. Apex: Acute. Base: Cordate. Margin: Entire. Texture and luster, upper and lower surfaces: Pubescent; matte. Color, upper and lower surfaces: Close to 146D.

*Peduncles*.—Length: About 5.4 cm. Diameter: About 1.5 mm. Angle: About 15° to 25° from stem axis. Strength: Strong, flexible. Texture and luster: Minute pubescence; matte. Color: Close to 146C.

*Reproductive organs*.—Androecium: Stamen number: About four. Filament length: About 4 mm. Filament color: Close to NN155B. Anther size: About 2 mm by 4 mm. Anther shape: Lanceolate. Anther color: Close to 155A. Amount of pollen: Scarce. Pollen color: Close to 155A. Gynoecium: Pistil number: One. Pistil length: About 1.7 cm. Style length: About 1.2 cm. Style color: Close to NN155C. Stigma appearance: Bi-parted. Stigma color: Close to NN155A. Ovary color: Close to 144A.

*Seeds and fruits*.—Seed and fruit development has not been observed on plants of the new *Thunbergia* to date.

Garden performance: Plants of the new *Thunbergia* have been observed to have good garden performance and to tolerate temperatures from about 2° C. to about 40° C. and are suitable for USDA Hardiness Zones 10 and 11.

Pathogen & pest resistance: Plants of the new *Thunbergia* have not been shown to be resistant to pathogens and pests common to *Thunbergia* plants.

It is claimed:

1. A new and distinct *Thunbergia* plant named 'DL1501' as illustrated and described.

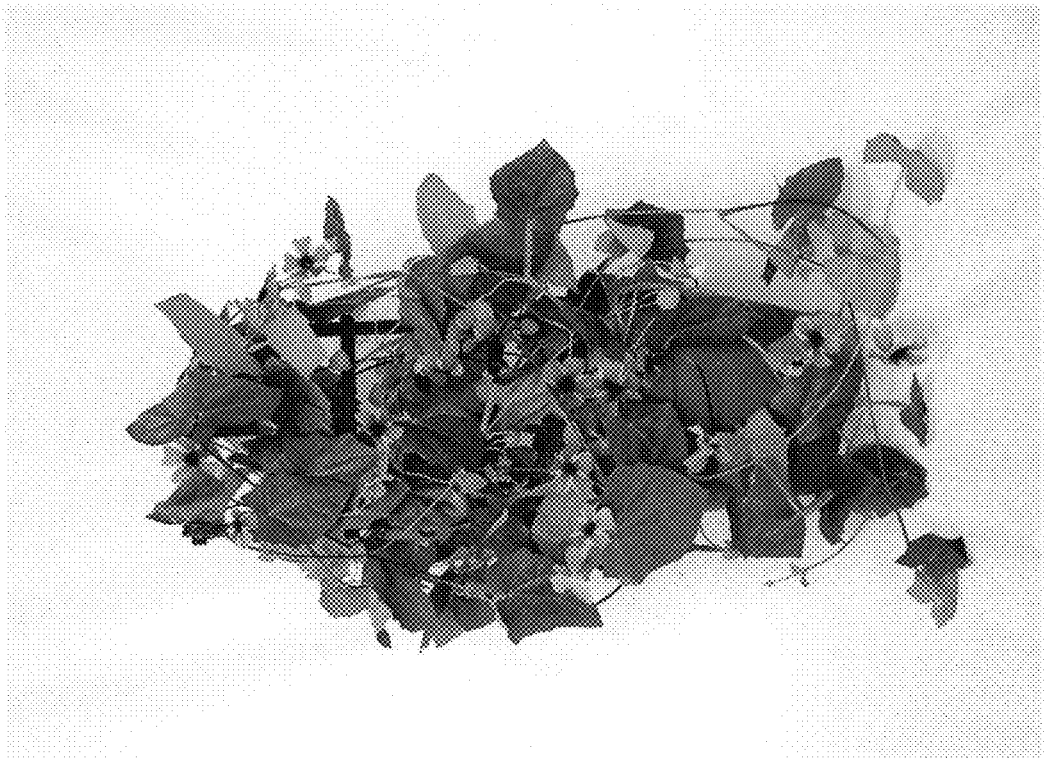
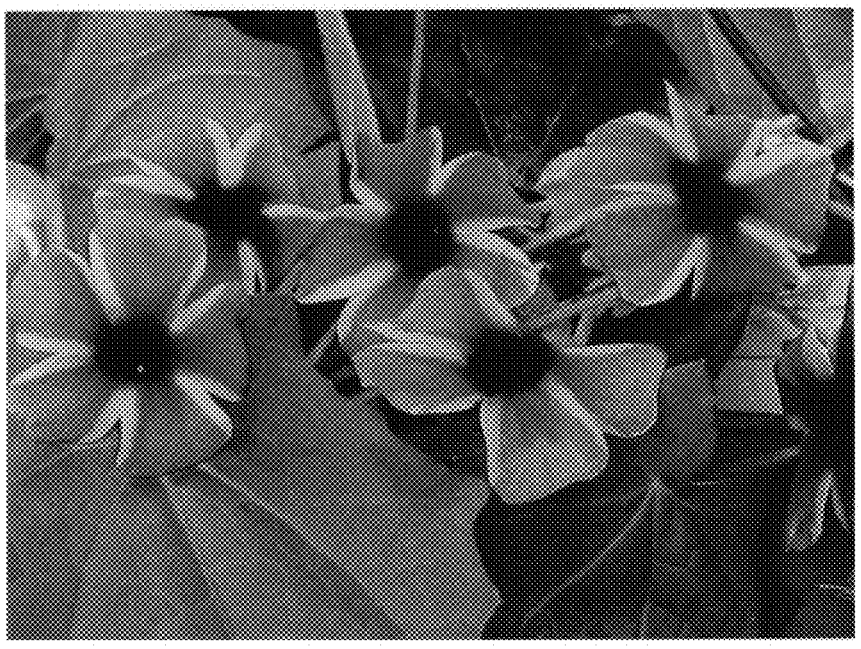

* * * * *